(12) United States Patent
Hojeibane

(10) Patent No.: US 7,842,077 B2
(45) Date of Patent: *Nov. 30, 2010

(54) BIFURCATED AXIALLY FLEXIBLE STENT

(75) Inventor: Hikmat Hojeibane, Princeton, NJ (US)

(73) Assignee: Cordis Corporation, Miami Lakes, FL (US)

( * ) Notice: Subject to any disclaimer, the term of this patent is extended or adjusted under 35 U.S.C. 154(b) by 1378 days.

This patent is subject to a terminal disclaimer.

(21) Appl. No.: 10/795,685

(22) Filed: Mar. 8, 2004

(65) Prior Publication Data

US 2004/0172126 A1     Sep. 2, 2004

Related U.S. Application Data

(60) Continuation of application No. 09/819,087, filed on Oct. 7, 1999, now Pat. No. 6,746,476, which is a division of application No. 09/028,383, filed on Feb. 24, 1998, now Pat. No. 6,017,363, which is a continuation-in-part of application No. 08/934,974, filed on Sep. 22, 1997, now Pat. No. 5,938,682.

(51) Int. Cl.
*A61F 2/06* (2006.01)
*A61M 29/00* (2006.01)

(52) U.S. Cl. .................................... 623/1.15; 623/1.35

(58) Field of Classification Search ............. 623/1.15, 623/1.11, 1.12, 1.13, 1.14, 1.16, 1.17, 1.18, 623/1.19, 1.2, 1.21, 1.42, 1.45, 1.46
See application file for complete search history.

(56) References Cited

U.S. PATENT DOCUMENTS

| | | | |
|---|---|---|---|
| 3,657,744 A | 4/1972 | Ersek | |
| 4,441,216 A | 4/1984 | Ionescu et al. | 3/1.5 |
| 4,503,569 A | 3/1985 | Dotter | |
| 4,553,545 A | 11/1985 | Maass et al. | |
| 4,580,568 A | 4/1986 | Gianturco | 128/345 |
| 4,733,665 A | 3/1988 | Palmaz | |
| 4,776,337 A | 10/1988 | Palmaz | |
| 4,800,882 A | 1/1989 | Gianturco | 128/343 |
| 4,856,516 A | 8/1989 | Hillstead | 128/343 |
| 4,886,062 A | 12/1989 | Wiktor | 128/343 |
| 4,907,336 A | 3/1990 | Gianturco | 29/515 |
| 4,969,458 A | 11/1990 | Wiktor | 606/194 |
| 4,990,131 A | 2/1991 | Dardik | 600/36 |

(Continued)

FOREIGN PATENT DOCUMENTS

DE     3205942 A1     9/1983

(Continued)

OTHER PUBLICATIONS

Dictionary.com Unabridged (v 1.1), Random House, Inc. http://dictionary.reference.com/browse/frequency (accessed: Sep. 18, 2008).

*Primary Examiner*—Vy Q Bui (57) ABSTRACT

A stent with axial flexibility, in a preferred embodiment, has a longitudinal axis and comprises a plurality of longitudinally disposed bands, wherein each band defines a generally continuous wave along a line segment parallel to the longitudinal axis. A plurality of links maintains the bands in a tubular structure. In a further embodiment of the invention, each longitudinally disposed band of the stent is connected, at a plurality of periodic locations, by a short circumferential link to an adjacent band. Further, a pair of bifurcated stents is disclosed.

4 Claims, 12 Drawing Sheets

U.S. PATENT DOCUMENTS

| | | | |
|---|---|---|---|
| 4,990,155 A | 2/1991 | Wilkoff | 606/191 |
| 4,994,071 A | 2/1991 | MacGregor | 606/194 |
| 5,015,253 A | 5/1991 | MacGregor | 623/1 |
| 5,035,706 A | 7/1991 | Gianturco | 606/198 |
| 5,041,126 A | 8/1991 | Gianturco | 606/195 |
| 5,064,435 A | 11/1991 | Porter | 623/12 |
| 5,102,417 A | 4/1992 | Palmaz | |
| 5,104,404 A | 4/1992 | Wolff | 612/1 |
| 5,108,415 A | 4/1992 | Pinchuk et al. | |
| 5,116,365 A | 5/1992 | Hillstead | 623/1 |
| 5,122,154 A | 6/1992 | Rhodes | 606/198 |
| 5,131,908 A | 7/1992 | Dardik et al. | 600/36 |
| 5,133,732 A | 7/1992 | Wiktor | 606/195 |
| 5,135,536 A | 8/1992 | Hillstead | 606/195 |
| 5,156,612 A | 10/1992 | Pinchuk et al. | |
| 5,163,958 A | 11/1992 | Pinchuk | 623/11 |
| 5,171,262 A | 12/1992 | MacGregor | 623/1 |
| 5,176,660 A | 1/1993 | Truckai | 604/282 |
| 5,178,618 A | 1/1993 | Kandarpa | 606/28 |
| 5,192,307 A | 3/1993 | Wall | 623/1 |
| 5,195,984 A | 3/1993 | Schatz | |
| 5,217,483 A | 6/1993 | Tower | 606/198 |
| 5,222,971 A | 6/1993 | Willard et al. | 606/158 |
| 5,246,445 A | 9/1993 | Yachia et al. | 606/108 |
| 5,258,021 A | 11/1993 | Duran | 623/2 |
| 5,266,073 A | 11/1993 | Wall | 623/1 |
| 5,275,622 A | 1/1994 | Lazarus et al. | 623/1 |
| 5,282,823 A | 2/1994 | Schwartz et al. | 606/198 |
| 5,282,824 A | 2/1994 | Gianturco | 606/198 |
| 5,290,305 A | 3/1994 | Inoue | |
| 5,292,331 A | 3/1994 | Boneau | 606/198 |
| 5,304,197 A | 4/1994 | Pinchuk et al. | |
| 5,304,200 A | 4/1994 | Spaulding | 606/198 |
| 5,314,444 A | 5/1994 | Gianturco | 606/195 |
| 5,314,472 A | 5/1994 | Fontaine | 623/12 |
| 5,334,301 A | 8/1994 | Heinke et al. | 204/267 |
| 5,342,387 A | 8/1994 | Summersq | 606/198 |
| 5,354,257 A | 10/1994 | Roubin et al. | 600/7 |
| 5,354,308 A | 10/1994 | Simon et al. | 606/198 |
| 5,356,423 A | 10/1994 | Tihon et al. | |
| 5,366,504 A | 11/1994 | Andersen et al. | 623/11 |
| 5,370,683 A | 12/1994 | Fontaine | 623/1 |
| 5,370,691 A | 12/1994 | Samson | 623/12 |
| 5,375,612 A | 12/1994 | Cottenceau et al. | 128/899 |
| 5,376,112 A | 12/1994 | Duran | 623/2 |
| 5,382,261 A | 1/1995 | Palmaz | 606/158 |
| 5,383,892 A | 1/1995 | Cardon et al. | |
| 5,387,235 A | 2/1995 | Chuter | 623/1 |
| 5,389,106 A | 2/1995 | Tower | 606/198 |
| 5,395,390 A | 3/1995 | Simon et al. | 606/198 |
| 5,397,355 A | 3/1995 | Marin et al. | 623/12 |
| 5,403,341 A | 4/1995 | Solar | 606/198 |
| 5,405,377 A | 4/1995 | Cragg | 623/1 |
| 5,411,549 A | 5/1995 | Peters | 623/1 |
| D359,802 S | 6/1995 | Fontaine | D24/155 |
| 5,421,955 A | 6/1995 | Lau et al. | |
| 5,423,885 A | 6/1995 | Williams | 623/1 |
| 5,441,515 A | 8/1995 | Khosravi et al. | 606/194 |
| 5,441,516 A | 8/1995 | Wang et al. | 606/198 |
| 5,443,477 A | 8/1995 | Marin et al. | 606/198 |
| 5,443,496 A | 8/1995 | Schwartz et al. | 623/1 |
| 5,443,498 A | 8/1995 | Fontaine | 623/1 |
| 5,443,500 A | 8/1995 | Sigwart | 623/1 |
| 5,449,372 A | 9/1995 | Schmaltz et al. | 606/198 |
| 5,449,373 A | 9/1995 | Pinchasik et al. | |
| 5,449,382 A | 9/1995 | Dayton | 623/1 |
| 5,496,365 A | 3/1996 | Sgro | |
| 5,527,354 A | 6/1996 | Fontaine et al. | |
| 5,569,295 A | 10/1996 | Lam | |
| 5,591,197 A | 1/1997 | Orth et al. | |
| 5,591,228 A | 1/1997 | Edoga | 623/1 |
| 5,591,229 A | 1/1997 | Parodi | 623/1 |
| 5,632,763 A | 5/1997 | Glastra | 606/194 |
| 5,643,312 A | 7/1997 | Fischell et al. | 606/198 |
| 5,649,952 A | 7/1997 | Lam | |
| 5,653,747 A | 8/1997 | Dereume | 623/1 |
| 5,669,924 A | 9/1997 | Shaknovich | 606/108 |
| 5,697,971 A | 12/1997 | Fischell et al. | |
| 5,700,286 A | 12/1997 | Tartaglia et al. | 623/1 |
| 5,720,735 A | 2/1998 | Dorros | 604/284 |
| 5,723,004 A | 3/1998 | Dereume et al. | 623/1 |
| 5,728,150 A | 3/1998 | McDonald et al. | 623/1 |
| 5,749,825 A | 5/1998 | Fischell et al. | 600/3 |
| 5,755,734 A | 5/1998 | Richter et al. | 606/194 |
| 5,755,771 A | 5/1998 | Penn et al. | 623/1 |
| 5,782,906 A | 7/1998 | Marshall et al. | 623/1 |
| 5,800,508 A | 9/1998 | Goicoechea et al. | 623/1 |
| 5,814,061 A | 9/1998 | Osborne et al. | 606/194 |
| 5,830,229 A | 11/1998 | Konya et al. | 606/198 |
| 5,861,027 A | 1/1999 | Trapp | 623/1 |
| 5,893,887 A | 4/1999 | Jayaraman | 623/1 |
| 5,895,405 A | 4/1999 | Inderbitzen | 606/194 |
| 5,906,640 A | 5/1999 | Penn et al. | 623/1 |
| 6,017,363 A | 1/2000 | Hojeibane | 623/1 |
| 6,183,509 B1 | 2/2001 | Dibia | 623/1.35 |
| 6,346,089 B1 | 2/2002 | Dibie | 603/1.15 |
| 2001/0039448 A1 | 11/2001 | Dibie | 623/1.16 |

FOREIGN PATENT DOCUMENTS

| | | |
|---|---|---|
| DE | 27708689 | 8/1997 |
| EP | 0 540 290 A2 | 10/1992 |
| EP | 0 662 307 A1 | 12/1994 |
| EP | 0 662 307 B1 | 12/1994 |
| EP | 0734698 B1 | 3/1996 |
| EP | 0 761 251 A1 | 4/1996 |
| EP | 0800801 A1 | 8/1996 |
| EP | 0830853 A1 | 7/1997 |
| EP | 0 832 616 A1 | 4/1998 |
| EP | 0 937 442 A2 | 8/1999 |
| EP | 0 938 878 A2 | 9/1999 |
| EP | 0 540 290 A3 | 10/1999 |
| EP | 0 950 386 | 10/1999 |
| FR | 0 566 807 A1 | 4/1992 |
| FR | 2678508 A1 | 1/1993 |
| FR | 2 733 682 A1 | 5/1995 |
| FR | 2 740 346 A1 | 4/1997 |
| GB | 1 205 743 | 9/1970 |
| JP | 1998043313 | 12/1989 |
| NL | C 1000180 | 12/1996 |
| WO | WO 96/03092 | 2/1996 |
| WO | WO96/26689 | 9/1996 |
| WO | WO 96/29955 A1 | 10/1996 |
| WO | WO 96/34580 | 11/1996 |
| WO | WO 96/34580 A1 | 11/1996 |
| WO | WO 97/15346 A1 | 5/1997 |
| WO | WO 97/16217 | 5/1997 |
| WO | WO 97/16217 A1 | 5/1997 |
| WO | WO97/25000 | 7/1997 |
| WO | WO 97/26840 A1 | 7/1997 |
| WO | WO 97/41803 A1 | 11/1997 |
| WO | WO 98/19628 | 5/1998 |
| WO | WO 98/36709 A1 | 8/1998 |
| WO | WO 98/47447 A1 | 10/1998 |
| WO | WO 99/08744 A1 | 2/1999 |

BIFURCATED AXIALLY FLEXIBLE STENT

CROSS REFERENCE

This application is a continuation and claims priority from U.S. application Ser. No. 09/819,087, filed Oct. 7, 1999, now U.S. Pat. No. 6,746,476 which is a division of U.S. Ser. No. 09/028,383, filed Feb. 24, 1998, now U.S. Pat. No. 6,017,363; which is a continuation-in-part of U.S. application Ser. No. 08/934,974, filed Sep. 22, 1997, now U.S. Pat. No. 5,938,682. For informational purposes Ser. No. 08/934,974 is a continuation-in-part of U.S. Application Ser. No. 60/010,686, filed Jan. 26, 1996, now abandoned; U.S. Application Ser. No. 60/017,479, filed Apr. 26, 1996, now abandoned; U.S. Application Ser. No. 60/017,415 filed May. 8, 1996, now abandoned; U.S. application Ser. No. 60/024,110, filed Aug. 16, 1996, now abandoned; and U.S. application Ser. No. 08/770,236, filed Dec. 20, 1996, all of which are incorporated herein by reference.

TECHNICAL FIELD

The present invention relates to a stent having axial flexibility and resilience in its expanded form.

BACKGROUND ART

A stent is commonly used as a tubular structure left inside the lumen of a duct to relieve an obstruction. Commonly, stents are inserted into the lumen in a non expanded form and are then expanded autonomously (or with the aid of a second device in situ. A typical method of expansion occurs through the use of a catheter mounted angioplasty balloon which is inflated within the stenosed vessel or body passageway in order to shear and disrupt the obstructions associated with the wall components of the vessel and to obtain an enlarged lumen.

In the absence of a stent, restenosis may occur as a result of elastic recoil of the stenotic lesion. Although a number of stent designs have been reported, these designs have suffered from a number of limitations. These include restrictions on the dimension of the stent such as describes a stent which has rigid ends (8 mm) and a flexible median part of 7-21 mm. This device is formed of multiple parts and is not continuously flexible along the longitudinal axis. Other stent designs with rigid segments and flexible segments have also been described.

Figure 1A:
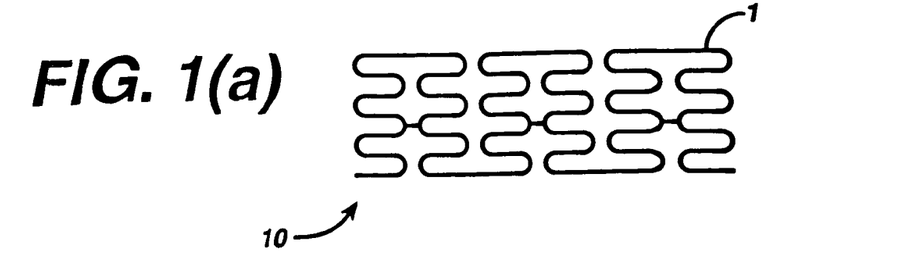
FIGS. 1(a) and 1(b) are side views of a stent having circumferentially disposed bands wherein the stent is in axially unbent and bent positions respectively, the latter showing protruding edges.
Figure 1B:
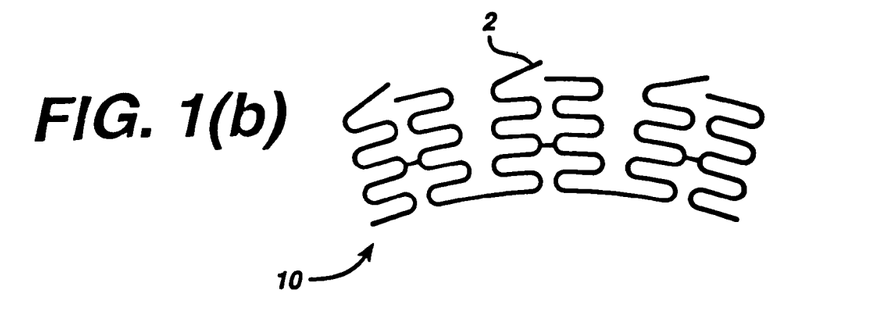

Other stents are described as longitudinally flexible but consist of a plurality of cylindrical elements connected by flexible members. This design has at least one important disadvantage, for example, according to this design, protruding edges occur when the stent is flexed around a curve raising the possibility of inadvertent retention of the stent on plaque deposited on arterial walls. This may cause the stent to embolize or more out of position and further cause damage to the interior lining of healthy vessels. (See FIG. 1(a) below).

Thus, stents known in the art, which may be expanded by balloon angioplasty, generally compromise axial flexibility to permit expansion and provide overall structural integrity.

SUMMARY OF THE INVENTION

The present invention overcomes some perceived shortcomings of prior art stents by providing a stent with axial flexibility. In a preferred embodiment, the stent has a first end and a second end with an intermediate section between the two ends. The stent further has a longitudinal axis and comprises a plurality of longitudinally disposed bands, wherein each band defines a generally continuous wave along a line segment parallel to the longitudinal axis. A plurality of links maintains the bands in a tubular structure. In a further embodiment of the invention, each longitudinally disposed band of the stent is connected, at a plurality of periodic locations, by a short circumferential link to an adjacent band. The wave associated with each of the bands has approximately the same fundamental spatial frequency in the intermediate section, and the bands are so disposed that the waves associated with them are spatially aligned so as to be generally in phase with one another. The spatially aligned bands are connected, at a plurality of periodic locations, by a short circumferential link to an adjacent band.

In particular, at each one of a first group of common axial positions, there is a circumferential link between each of a first set of adjacent pairs of bands.

At each one of a second group of common axial positions, there is a circumferential link between each of a second set of adjacent rows of bands, wherein, along the longitudinal axis, a common axial position occurs alternately in the first group and in the second group, and the first and second sets are selected so that a given band is linked to a neighboring band at only one of the first and second groups of common axial positions.

In a preferred embodiment of the invention, the spatial frequency of the wave associated with each of the bands is decreased in a first end region lying proximate to the first end and in a second end region lying proximate to the second end, in comparison to the spatial frequency of the wave in the intermediate section. In a further embodiment of the invention, the spatial frequency of the bands in the first and second end regions is decreased by 20% compared with the spatial frequency of the bands in the intermediate section. The first end region may be located between the first end and a set of circumferential links lying closest to the first end and the second end region lies between the second end and a set of circumferential links lying closest to the second end. The widths of corresponding sections of the bands in these end regions, measured in a circumferential direction, are greater in the first and second end regions than in the intermediate section. Each band includes a terminus at each of the first and second ends and the adjacent pairs of bands are joined at their termini to form a closed loop.

In a further embodiment of the invention, a stent is provided that has first and second ends with an intermediate section therebetween, the stent further having a longitudinal axis and providing axial flexibility. This stent includes a plurality of longitudinally disposed bands, wherein each band defines a generally continuous wave having a spatial frequency along a line segment parallel to the longitudinal axis., the spatial frequency of the wave associated with each of the bands being decreased in a first end region lying proximate to the first end and in a second end region lying proximate to the second end, in comparison to the spatial frequency of the wave in the intermediate section; and a plurality of links for maintaining the bands in a tubular structure. The first and second regions have been further defined as the region that lies between the first and second ends and a set of circumferential links lying closest to the first end and second end.

In a further embodiment the widths of the sectionals of the bands, measured in a circumferential direction, are greater in the first and second end regions than in the intermediate section.

In yet an additional embodiment, the stent is divided into a group of segments, and each of the segments are connected by a flexible connector. In addition, the stent segments are provided with enhanced flexibility at the flexible connectors, due to the geometrical configuration of the flexible connectors.

Furthermore, the current stent can be modified to provide for bifurcated access, whereas the stent itself is uniform throughout. If the manufacturer designs such a stent to have an essential opening, then it is possible to place the stent such that a pair of stents can be placed one through the other. In this fashion, the stents are capable of being placed at a bifurcation, without any welding or any special attachments. The interlocking mechanism can be incorporated into the stent design to cause the stent to interlock at the desired position during assembly of the device.

BRIEF DESCRIPTION OF THE DRAWINGS

The foregoing aspects of the invention will be more readily understood by reference to the following detailed description, taken with the accompanying drawings, in which.

DETAILED DESCRIPTION OF SPECIFIC EMBODIMENTS

Improvements afforded by embodiments of the present invention include (a) increased flexibility in two planes of the non-expanded stent while maintaining radial strength and a high percentage open area after expansion; (b) even pressure on the expanding stent that ensures the consistent and continuous contact of expanded stent against artery wall; (c) avoidance of protruding parts during bending; (d) removal of existing restrictions on maximum of stent; and reduction of any shortening effect during expansion of the stent.

In a preferred embodiment of the invention, an expandable cylindrical stent 10 is provided having a fenestrated structure for placement in a blood vessel, duct or lumen to hold the vessel, duct or lumen open, more particularly for protecting a segment of artery from restenosis after angioplasty. The stent 10 may be expanded circumferentially and maintained in an expanded configuration, that is circumferentially rigid. The stent 10 is axially flexible and when flexed at a band, the stent 10 avoids any externally protruding component parts.

FIG. 1 shows what happens to a stent 10, of a similar design to a preferred embodiment herein but utilizing instead a series of circumferentially disposed bands, when caused to bend in a manner that is likely encountered within a lumen of the body. A stent 10 with a circumferential arrangement of bands (1) experiences an effect analogous to a series of railroad cars on a track. As the row of railroad cars proceeds around the bend, the corner of each car proceeding around the bend after the coupling is caused to protrude from the contour of the track. Similarly, the serpentine circumferential bands have protrusions (2) above the surface of the stent 10 as the stent 10 bends.

Figure 1C:
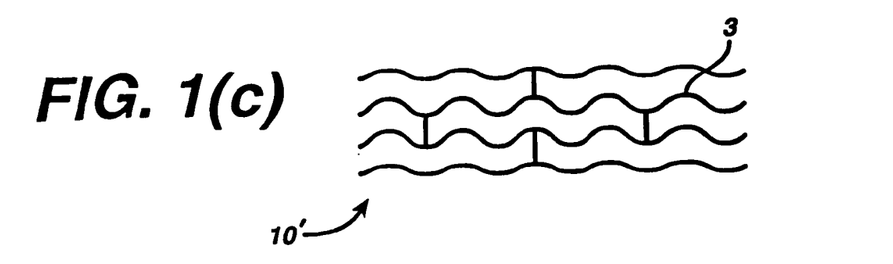
FIGS. 1(c) and 1(d) are side views of an axially flexible stent in accordance with the present invention wherein the stent is in unbent and bent positions respectively, the latter displaying an absence of protruding edges.
Figure 1D:
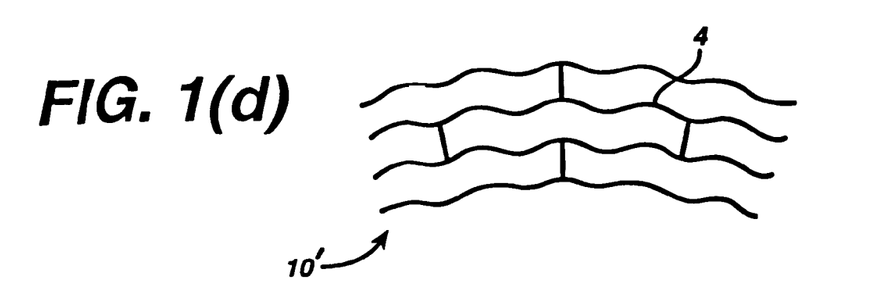
Figure 7:
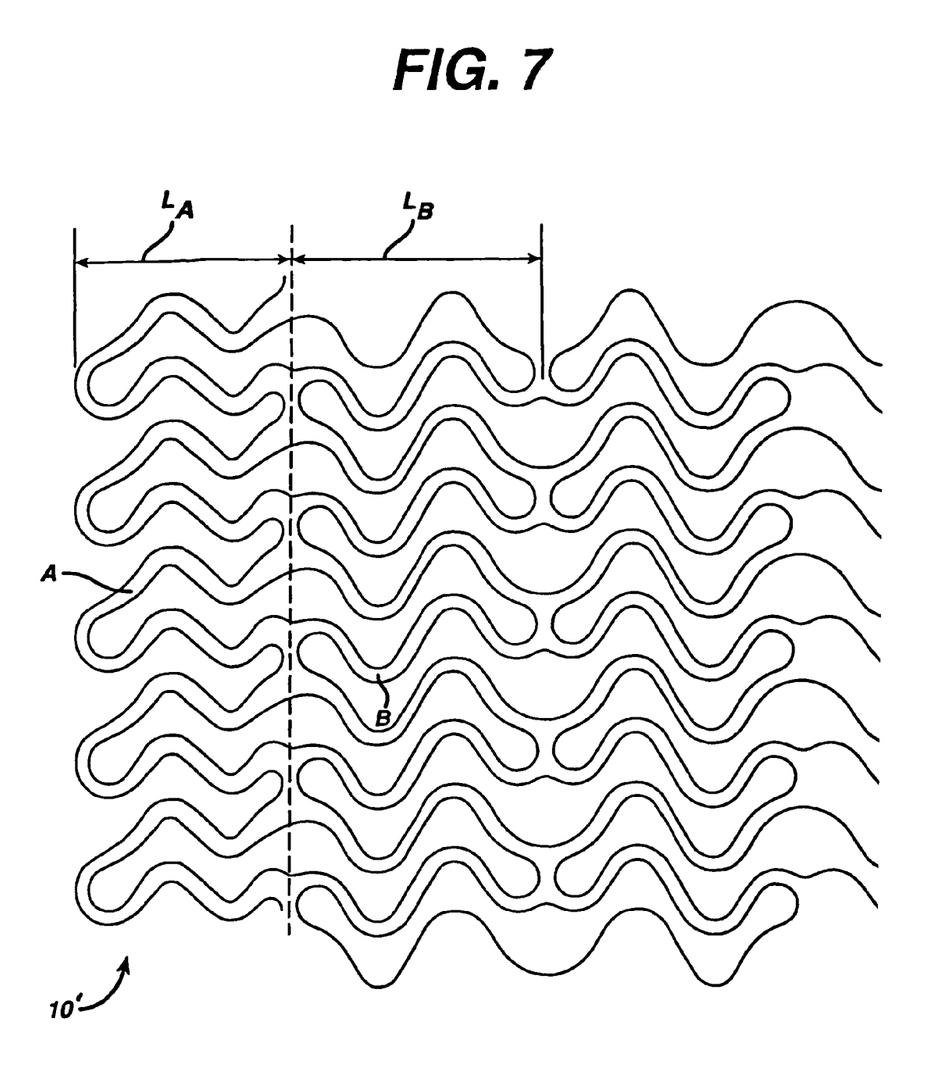
FIG. 7 shows a two dimensional layout of the stent. The ends are modified such that the length ($L_A$) is about 20% shorter than length ($L_B$) and the width of the band A is greater than the width of band B.

In contrast, the novel design of the embodiment shown in FIGS. 1(c) and 1(d) and FIG. 7 in which the bands (3) are axially flexible and are arranged along the longitudinal axis, avoids such an effect when the stent 10 is bent, so the bent bands (4) do not protrude from the profile of the curve of the stent 10. Furthermore, any flaring at the ends of the stent 10 that might occur with a stent 10 having a uniform structure is substantially eliminated by introducing a modification at the ends of the stent 10. This modification comprises decreasing the spatial frequency and increasing the width of the corresponding bands in a circumferential direction ($L_A$ and A) compared to that of the intermediate section. ($L_B$ and B).

In an embodiment of the invention, the spatial frequency $L_A$ may be decreased 0-50% with respect to $L_B$, and the width A may be increased in the range of 0-150% with respect to B. Other modifications at the ends of the stent 10 may include increasing the thickness of the wall of the stent 10 and selective electropolishing. These modifications protect the artery and any plaque from abrasion that may be caused by the stent 10 ends during insertion of the stent 10. The modification also may provide increased radio-opacity at the ends of the stent 10. Hence it may be possible to more accurately locate the stent 10 once it is in place in the body.

Figure 2:
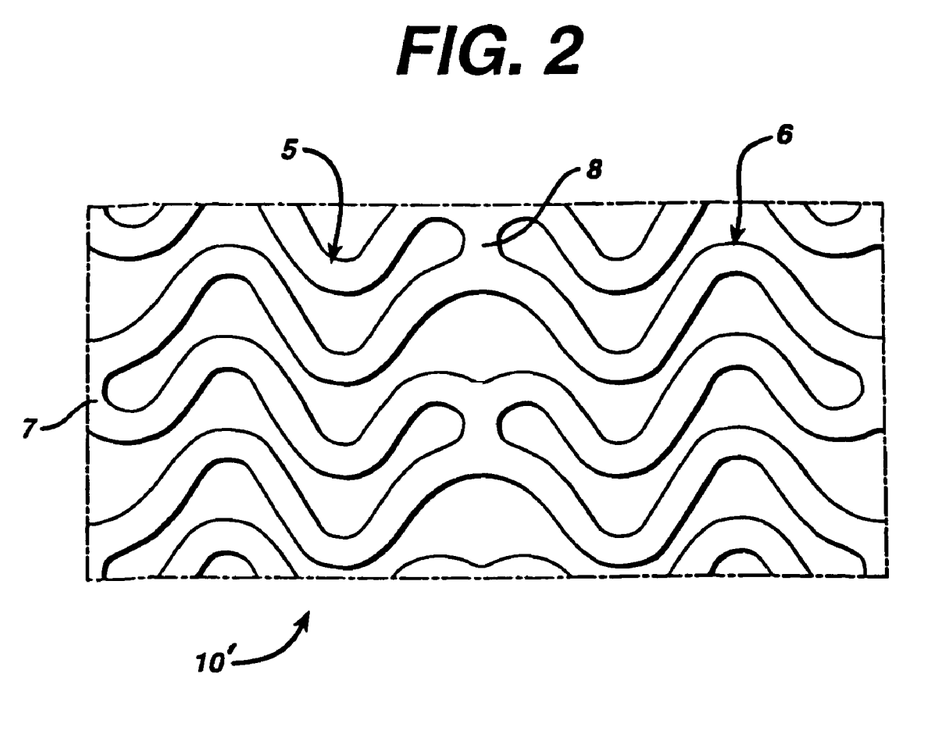
FIG. 2 is a side view of a portion of the stent of FIGS. 1(c) and 1(d) showing the longitudinal bands, spaces, and inner radial measurements of bends in the bands being measured in inches.
Figure 6:
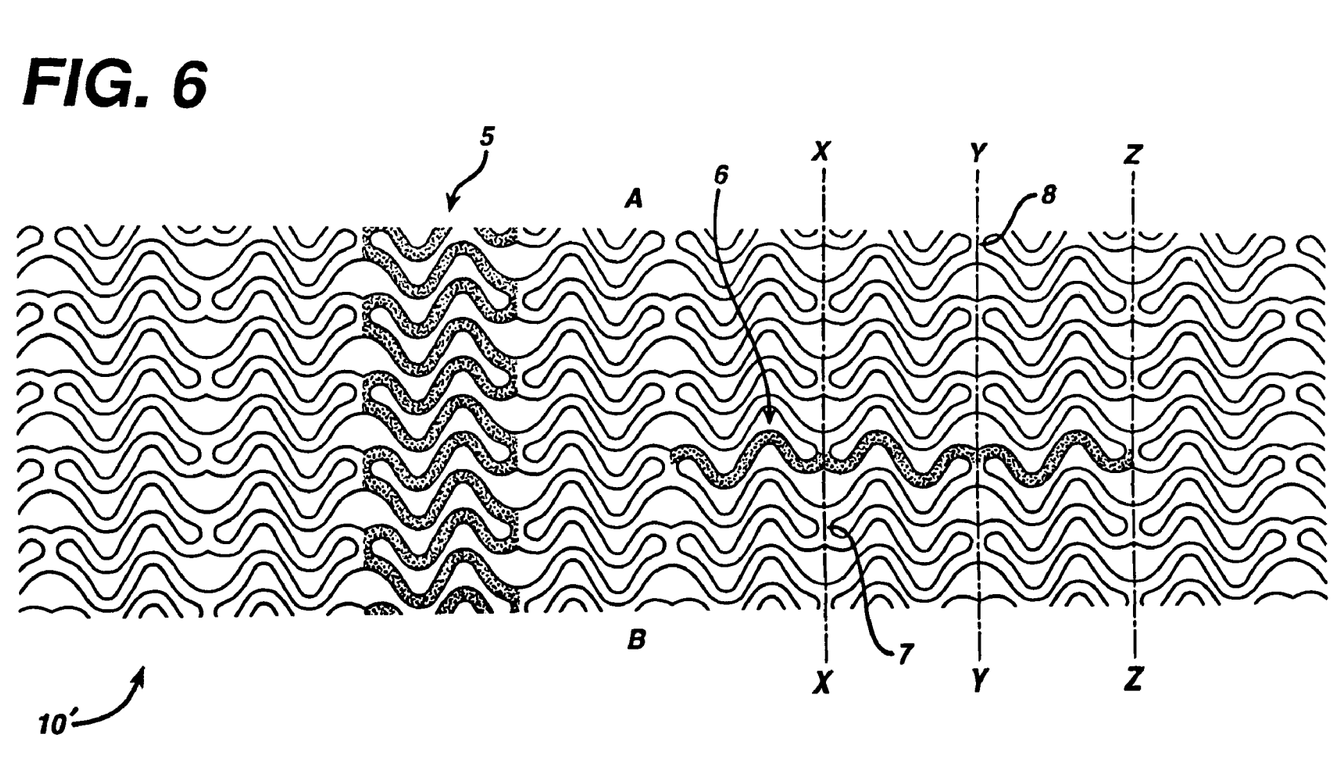
FIG. 6 shows a two-dimensional layout of the stent of FIG. 4 to form a cylinder such that edge "A" meets edge "B", and illustrating the spring-like action provided in circumferential and longitudinal directions.

The embodiment as shown in FIGS. 2 and 6 has the unique advantage of possessing effective "springs" in both circumferential and longitudinal directions shown as items (5) and (6) respectively. These springs provide the stent 10 with the flexibility necessary both to navigate vessels in the body with reduced friction and to expand at the selected site in a manner that provides the final necessary expanded dimensions without undue force while retaining structural resilience of the expanded structure.

Figure 4:
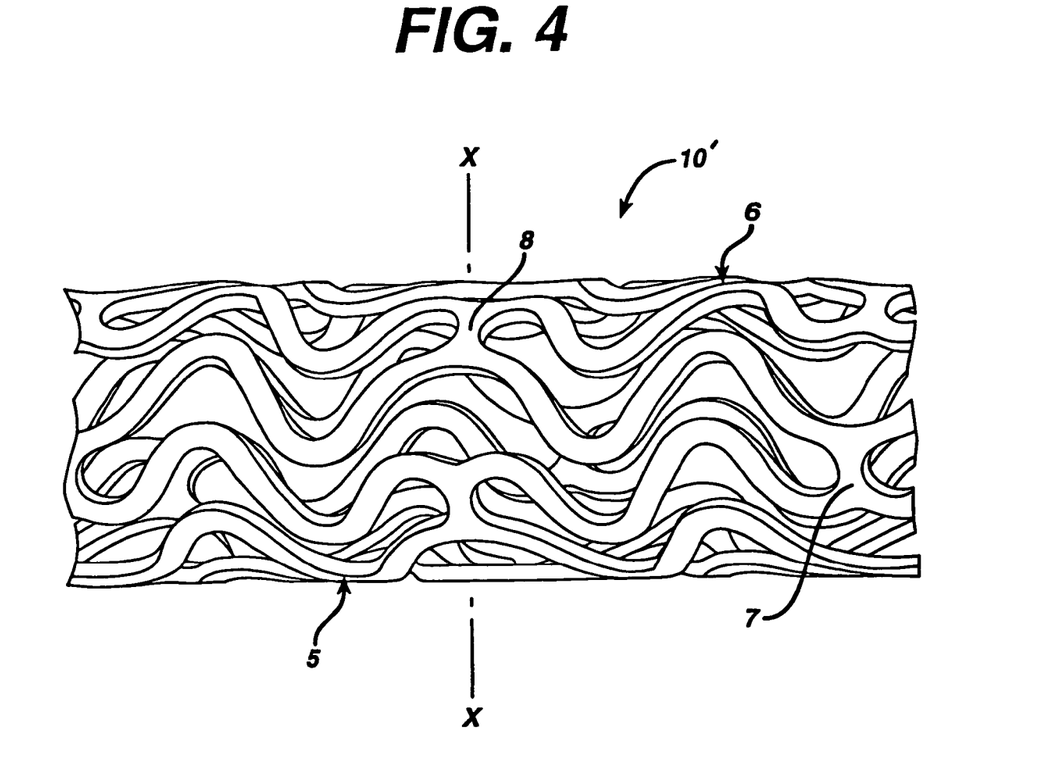
FIG. 4 is a view along the length of a piece of cylindrical stent (ends not shown) prior to expansion showing the exterior surface of the cylinder of the stent and the characteristic banding pattern.
Figure 5:
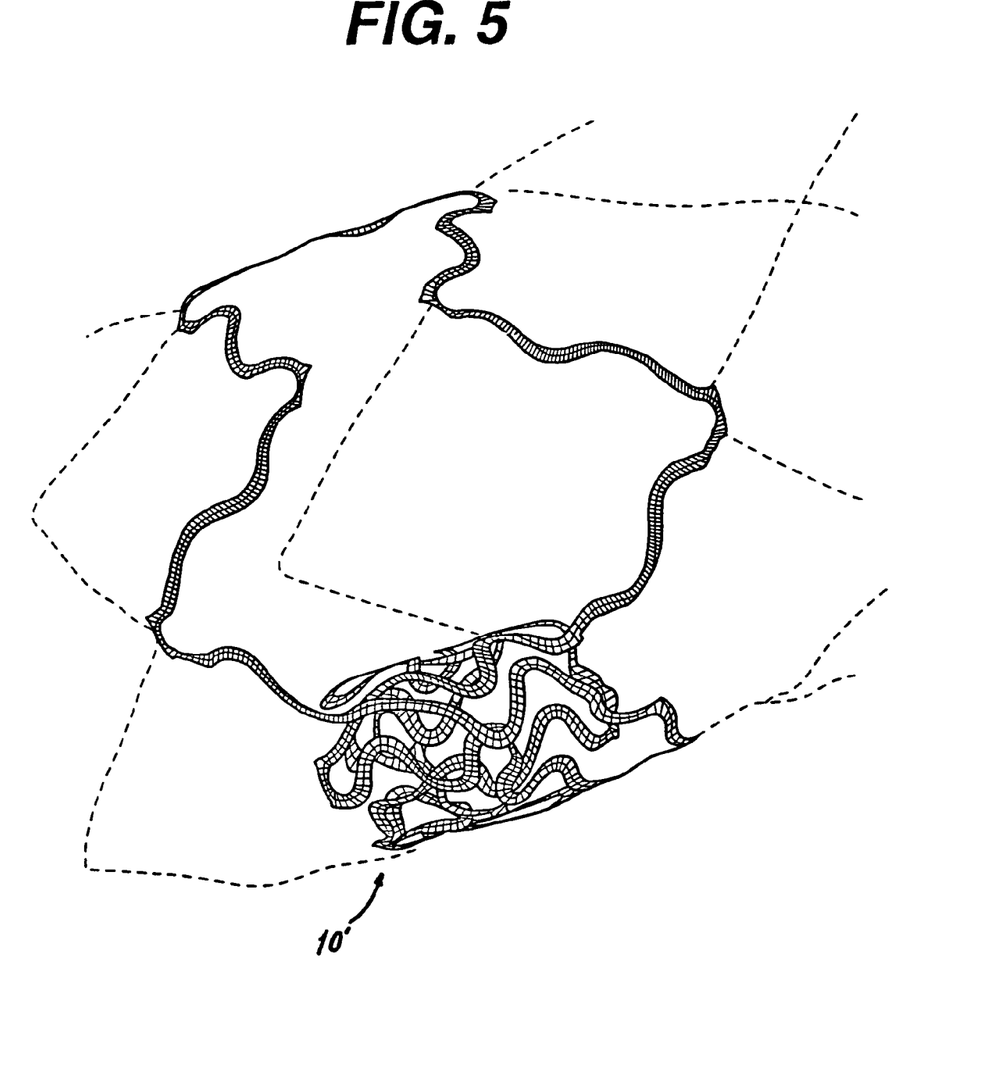
FIG. 5 is an isometric view of a deflection plot where the stent of FIG. 2 is expanded to a larger diameter of 5 mm.

As shown in both FIGS. 2, 4 and 6, each longitudinal band undulates through approximately two cycles before there is formed a circumferential link to an adjacent band. Prior to expansion, the wave W associated with each of the bands may have approximately the same fundamental spatial frequency, and the bands are so disposed that the wave W associated with them are spatially aligned, so as to be generally in phase with one another as shown in FIG. 6.

The aligned bands on the longitudinal axis are connected at a plurality of periodic locations, by a short circumferential link to an adjacent band. Consider a first common axial position such as shown by the line X-X in FIGS. 4 and 6. Here an adjacent pair of bands is joined by circumferential link 7. Similarly other pairs of bands are also linked at this common axial position. At a second common axial position, shown in FIG. 6 by the line Y-Y, an adjacent pair of bands is joined by circumferential link 8. However, any given pair of bands that is linked at X-X is not linked at Y-Y and vice-versa. The X-X pattern of linkages repeats at the common axial position Z-Z. In general, there are thus two groups of common axial positions. In each of the axial positions of any one group are links between the same pairs of adjacent bands, and the groups alternate along the longitudinal axis of the embodiment. In this way, circumferential spring 6 and the longitudinal spring 6 are provided.

Figure 3A:
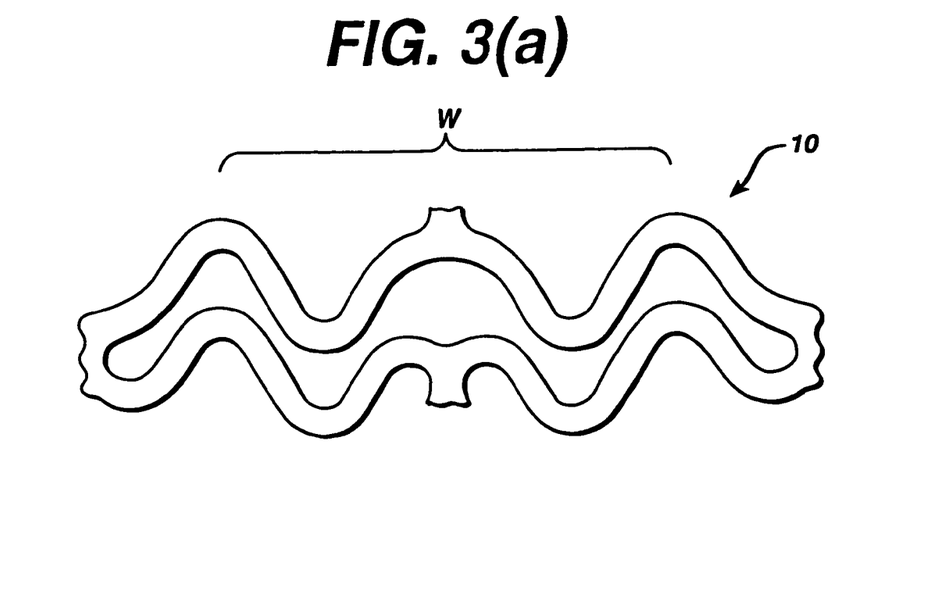
FIGS. 3(a) and 3(b) show a portion of the stent of FIG. 2 with two bands between two circumferential links (a) before expansion in the undeformed state; and (b) after expansion, in the deformed state.
Figure 3B:
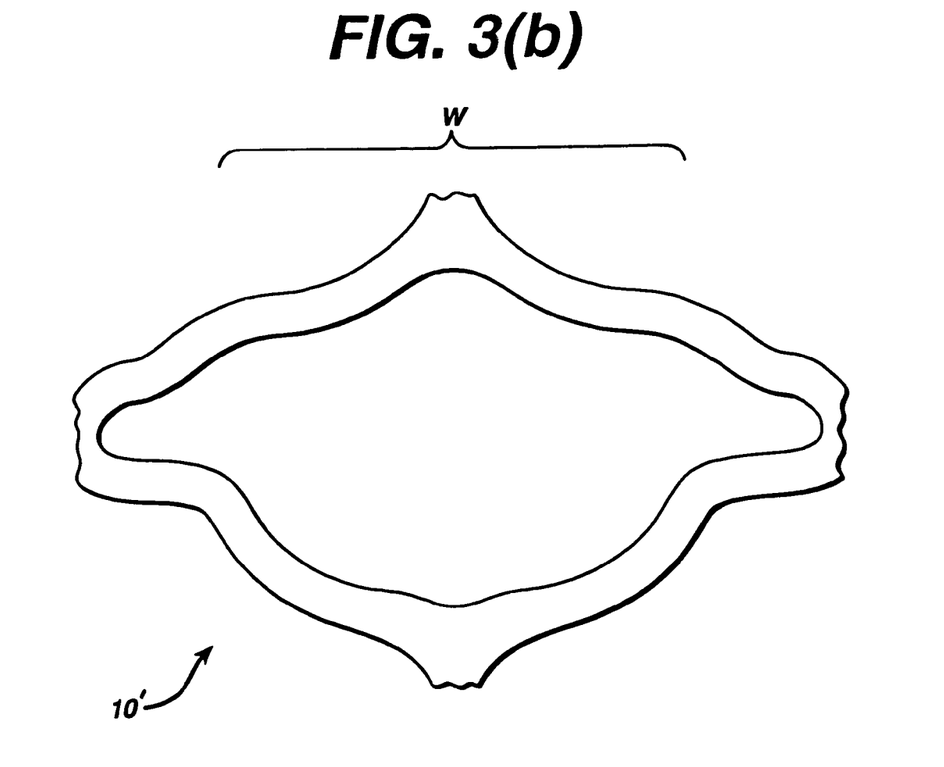

A feature of the expansion event is that the pattern of open space in the stent 10 of the embodiment of FIG. 2 before expansion is different from the pattern of the stent 10 after expansion. In particular, in a preferred embodiment, the pattern of open space on the stent 10 before expansion is serpentine, whereas after expansion, the pattern approaches a diamond shape (3a, 3b). In embodiments of the invention, expansion may be achieved using pressure from an expanding balloon or by other mechanical means.

In the course of expansion, as shown in FIG. 3, the wave W shaped bands tend to become straighter. When the bands become straighter, they become stiffer and thereby withstand relatively high radial forces. FIG. 3 shows how radial expansion of the stent 10 causes the fenestra to open up into a diamond shape with maximum stress being expended on the apices of the diamond along the longitudinal axis. When finite element analyses including strain studies were performed on the stent 10, it was found that maximum strain was experienced on the bands and links and was below the maximum identified as necessary to maintain structural integrity.

The optimization of strain of the stent 10 is achieved by creating as large a turn radius as possible in the wave W associated with each band in the non-expanded stent 10. This is accomplished while preserving a sufficient number of bands and links to preserve the structural integrity of the stent 10 after expansion. In an embodiment of the invention, the strain may be less than 0.57 inches/inch for 316 L stainless steel. The expansion pressure may be 1.0-7.0 atmospheres. The number of bands and the spatial frequency of the wave W on the longitudinal axis also affects the number of circumferential links. The circumferential links contribute structural integrity during application of radial force used in expansion of the stent 10 and in the maintenance of the expanded form. While not being limited to a single set of parameters, an example of a stent 10 of the invention having a longitudinal axis and providing axial flexibility of the type shown in FIG. 6, may include a stent 10 having an expanded diameter of 4 mm and a length of 30 mm that for example may have about 8-12 rows, more particularly 10 rows and about 6-10 slots, more particularly 8 slots (a slot is shown in FIG. 6 as extending between X and Z), with a wave W amplitude of about ¼-¹⁄₁₀ of a slot length, more particularly ⅛ of a slot length.

The stent 10 may be fabricated from many methods. For example, the stent 10 may be fabricated from a hollow or formed stainless steel tube that may be cut out using lasers, electric discharge milling (EDM), chemical etching or other means. The stent 10 is inserted into the body and placed at the desired site in an unexpanded form. In a preferred embodiment, expansion of the stent 10 is effected in a blood vessel by means of a balloon catheter, where the final diameter of the stent 10 is a function of the diameter of the balloon catheter used.

In contrast to stents of the prior art, the stent 10 of the invention can be made at any desired length, most preferably at a nominal 30 mm length that can be extended or diminished by increments, for example 1.9 mm increments.

It will be appreciated that a stent 10 in accordance with the present invention may be embodied in a shape memory material, including, for example, an appropriate alloy of nickel and titanium; or stainless steel. In this embodiment after the stent 10 has been formed, it may be compressed so as to occupy a space sufficiently small as to permit its insertion in a blood vessel or other tissue by insertion means, wherein the insertion means include a suitable catheter, or flexible rod. On emerging from the catheter, the stent 10 may be configured to expand into the desired configuration where the expansion is automatic or triggered by a change in pressure, temperature or electrical stimulation.

An embodiment of the improved stent 10 has utility not only within blood vessels as described above but also in any tubular system of the body such as the bile ducts, the urinary system, the digestive tube, and the tubes of the reproductive system in both men and women.

Figure 8:
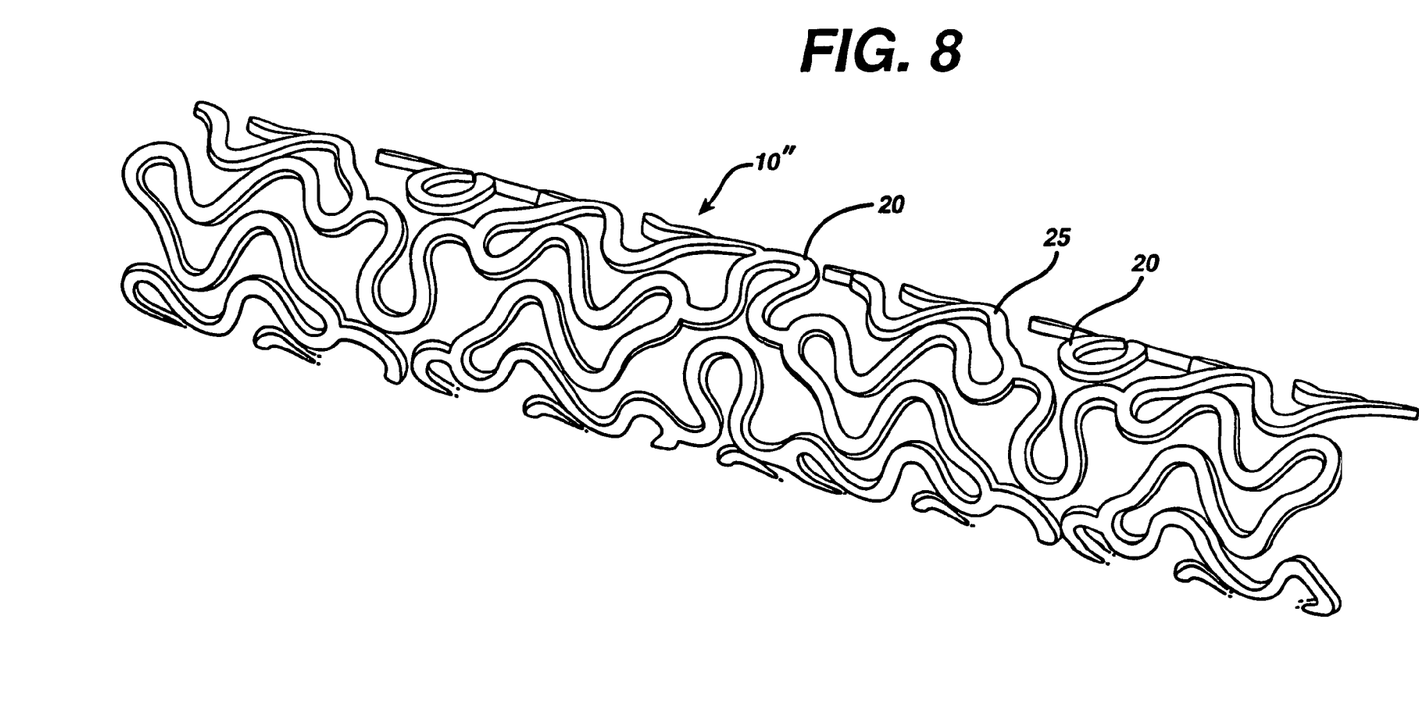
FIG. 8 shows a perspective view of a stent containing flexible connectors as described in the present invention.
Figure 9:
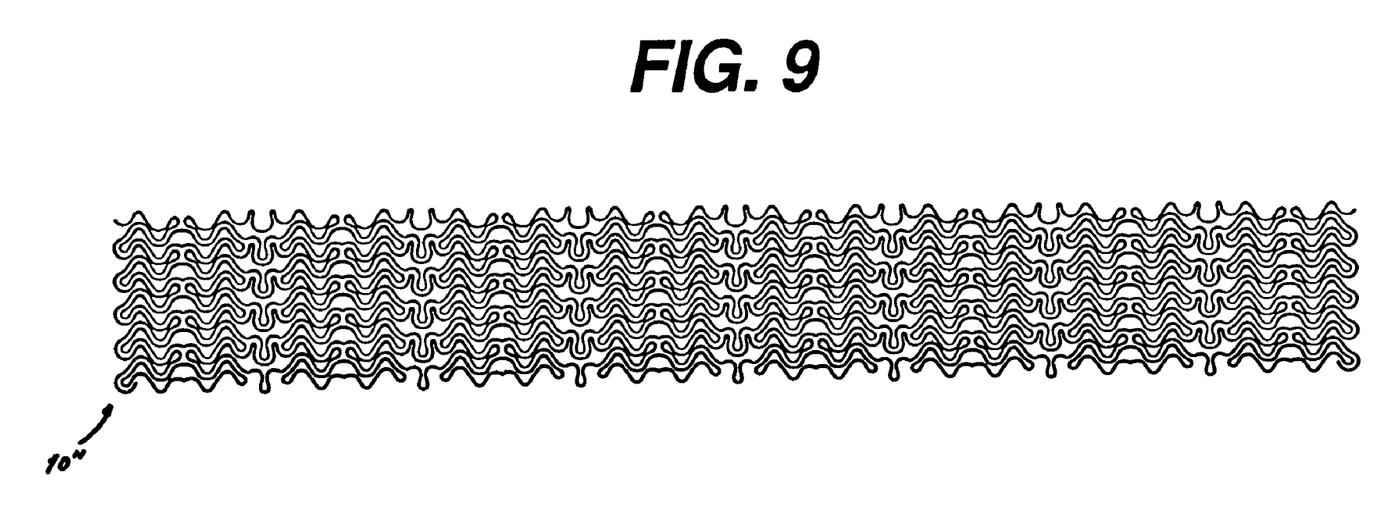
FIG. 9 shows a stent in which the flexible connectors are attached to stent segments, in layout form. These flexible connectors are attached in an every-other-segment pattern.
Figure 10:
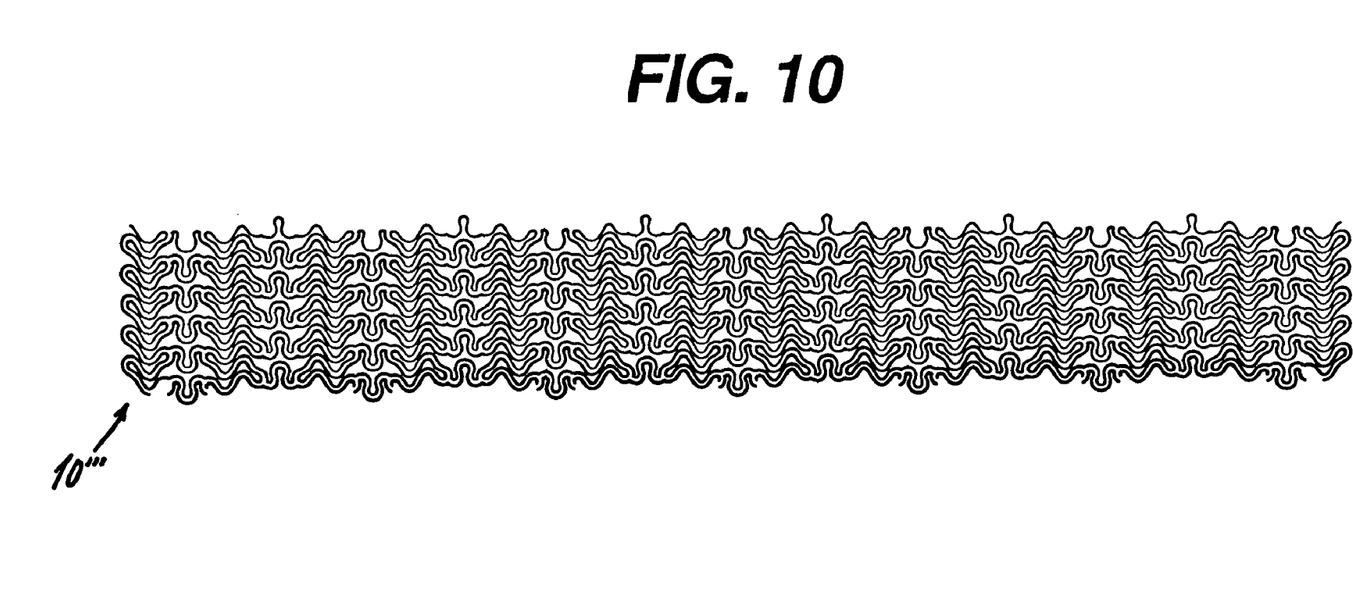
FIG. 10 shows a layout view where the stent segments are connected with a flexible connector in every stent segment pattern.
Figure 11:
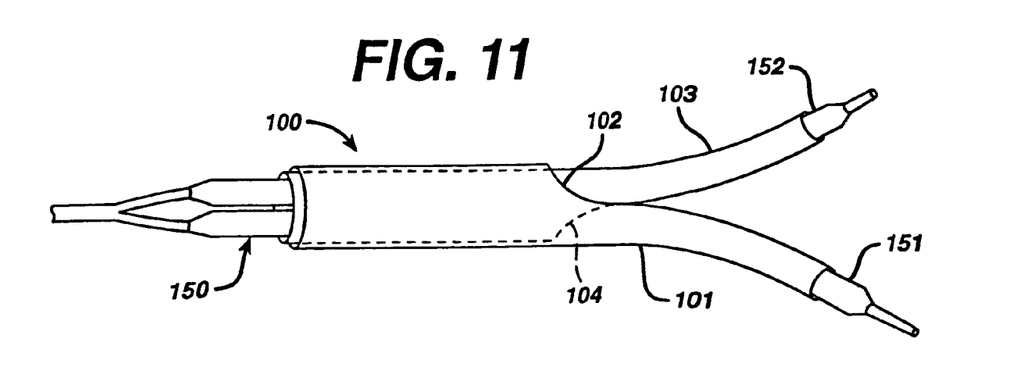
FIG. 11 shows a schematic of the unexpanded stents when loaded on the stent delivery system.
Figure 12:
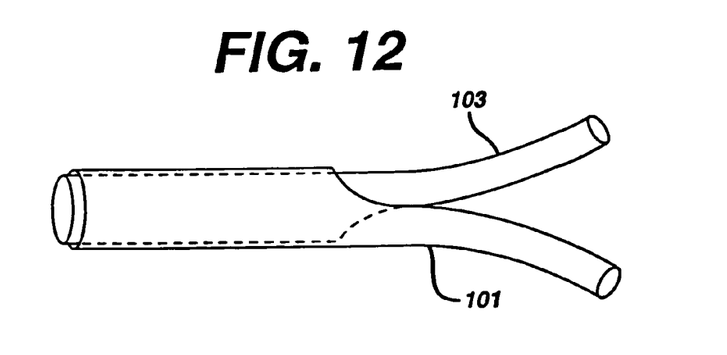
FIG. 12 shows the stents placed alone.

In yet a further embodiment, there is described a stent 10 as presently disclosed containing a multiplicity of curvilinear segments 20. These curvilinear segments 20 are connected to each other via a generally perpendicular connector 25. The generally perpendicular connector 25 lies substantially in the plane perpendicular to the longitudinal axis of the stent 10. Each of the stent 10 segments as described herein is connected to an adjacent stent 10 segment. This is done using a series of flexible connectors. Importantly, the connectors themselves can be made narrower at their midpoints. This enhances the possibility of flexure at that point. Of course, it is to be realized that alternate designs of the connector to insure flexibility are possible, and contemplated by this invention.

In essence therefore, the stent 10 as described in FIG. 8 is a stent 10 of considerable flexibility when compared to more rigid rectilinear stents. Nonetheless, the stent 10 of the present invention does not depart from the basic concepts set forth herein, in that it discloses a continuously curvilinear strut. This curvilinear strut is connected to other curvilinear struts via a series of "second" more flexible connectors, described above.

In any regard, it can be seen that the stent 10 of the present invention incorporates various new and useful members. One of them is the flexible connector in conjunction with a generally curvilinear stent. Another is the use of the generally larger struts at the ends of the stent 10 in order to provide for continued support at the stent 10 ends. A final aspect is the use of flexible connectors amongst stent 10 segments to provide for greater flexibility.

In all regards, however, it is to be seen that the present invention is to be determined from the attached claims and their equivalents.

As can be seen from FIGS. 11 through 14, an improved device 100 of the present invention can also be made to perform in a bifurcated fashion. In this way, the stent 101 contains a central opening 102. This central opening 102 allows for the passage of an unexpanded stent 103 of the same size. Typically of course, the two stents 101, 103 will have the same general configuration, and one can pass through the other on the same type of diameter balloon. In fact, the balloon 150 as seen in the current FIGS. 11-16 is a bifurcated balloon, but need not be. Two separate balloons are certainly capable of performing the same function. The balloons are preferably less than 6 Fr in their unexpanded shape in a preferred embodiment, but of course, need not be so constrained.

As seen in FIGS. 11-14, the first stent 101 (the lower one in the figure) is loaded on one of the balloons 151. It has an opening 102 central to it. This opening faces the upper stent 103 and balloon 152, the upper stent 102 loaded on the second balloon 152. The upper stent 103, when loaded on the second balloon 152 also has an opening 104 which faces the lower stent 101. In this fashion, as the second stent 103 is strung through the first stent 101, it is placed in such a fashion so as to have a mutually facing contact with the first stent 101. Then, as the balloon and stent combination is guided through the human anatomy, the devices will go toward a bifurcation. When this happens, the device is caused to split using various guide wire techniques. Then, each of the respective balloons are inflated.

Figure 13:
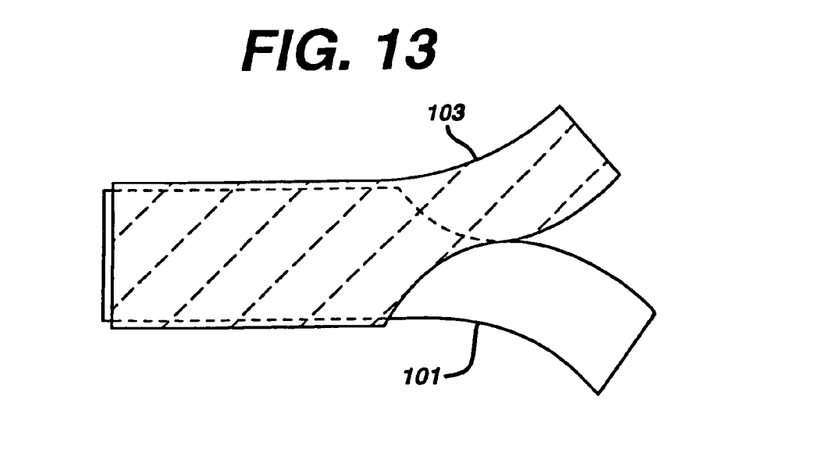
FIG. 13 shows the stents as expanded without the delivery system.
Figure 14:
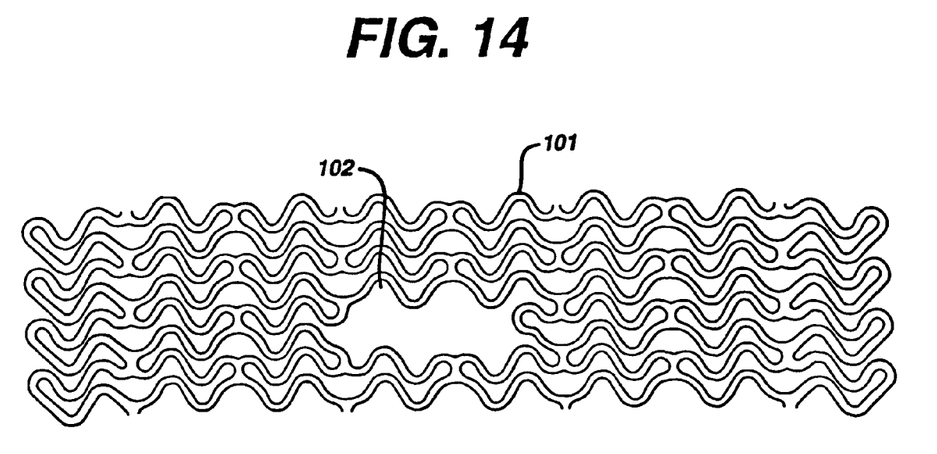
FIG. 14 shows a modification of the stent in a layout view.

On this inflation, the entire device is expanded such as seen in FIG. 13. Thus, the entire bifurcation is covered, and yet in a much easier than typical bifurcated expansions. What is unique is that there is no welding of the stents 101, 103 together, they can be common "off-the-shelf" stents modified only slightly so as to be useful for this particular need.

It should be noted that the stent of FIGS. 11-14 can be designed with any slot or wire configurations or of any high density materials or composites and can be balloon expandable or self-expanding or even the combination of both. The devices can be sold separately from separate catheters to be assembled during the desired procedure by the clinicians; can be used with a bifurcated balloon or two separate balloons; or incorporated with one or more radio-opaque markers to allow for better positioning in radioopacity. The bifurcated stent delivery system is placed by crimping over two balloons and then expanded at the sight of the lesion.

What is claimed is:

1. A bifurcated stent comprising:

a first stent portion having first and second ends with an intermediate section therebetween, the stent further having a longitudinal axis and a plurality of longitudinally disposed cells, each of the cells having struts formed in the shape of waves, said waves having a spatial frequency along the length of the stent wherein each cell has an opening therein; and a second stent portion having first and second ends with an intermediate section therebetween, the stent further having a longitudinal axis and a plurality of longitudinally disposed cells, wherein each cell has an opening therein; and each of said stent portions capable of expanding from a first respective diameter to a larger second respective diameter; and wherein said second stent portion is configured in its said first respective diameter to pass through a cell of the first stent portion; and wherein the spatial frequency of the wave associated with each of the struts in the first stent portion is decreased in a first end region lying proximate to the first end and in a second end region lying proximate to the second end, in comparison to the spatial frequency of the wave in the intermediate section, by a factor of as great as twenty percent.

2. A stent according to claim 1, each stent portion formed by a series of said struts connected by links, wherein each link is axially displaced from any circumferentially adjacent link.

3. A stent according to claim 2, wherein, at each one of a first group of common axial positions, there is a link between a first set of adjacent pairs of struts.

4. A stent according to claim 3, wherein, at each one of a second group of common axial positions, there is a link between a second set of adjacent sets of struts, wherein, along the longitudinal axis, a common axial position occurs alternately in the first group and in the second group, and the first and second sets are selected so that a given strut is linked to a neighboring strut at only one of the first and second groups of common axial positions.

\* \* \* \* \*